US00PP34715P2

(12) United States Plant Patent
Hansen

(10) Patent No.: US PP34,715 P2
(45) Date of Patent: Nov. 1, 2022

(54) ***MONARDA* PLANT NAMED 'BERRY TAFFY'**

(50) Latin Name: ***Monarda* hybrid**
Varietal Denomination: Berry Taffy

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/300,434

(22) Filed: Jun. 29, 2021

(51) Int. Cl.
*A01H 5/02* (2018.01)
*A01H 6/50* (2018.01)

(52) U.S. Cl.
USPC ..... Plt./455
CPC ..... *A01H 6/50* (2018.05)

(58) Field of Classification Search
USPC ..... Plt./455
CPC ..... A01H 5/02
See application file for complete search history.

*Primary Examiner* — Kent L Bell

(57) ABSTRACT

The new and distinct cultivar of ornamental cultivar of hybrid ornamental Bee Balm plant named *Monarda* 'Berry Taffy' with deep-green, highly-glossy, powdery mildew-tolerant foliage that emerges with moderate to strong anthocyanin blushing and mature to deep green and flower heads of hot raspberry-pink flowers. The bracts subtending inflorescences have deep reddish and wine coloration. The plant habit is compact and winter-hardy, useful in the landscape as a specimen, en masse, or as a containerized plant.

1 Drawing Sheet

Botanical designation and cultivar denomination:
Botanical classification: *Monarda* hybrid.
Variety denomination: 'Berry Taffy'.

STATEMENT REGARDING PRIOR DISCLOSURES UNDER 37 CFR 1.77(B)(6)

The first public disclosure of the claimed plant, in the form of a sale, was made by Walters Gardens, Inc. on Jun. 29, 2020. Prior to that, on Feb. 1, 2020 the claimed plant was displayed with a non-enabling photograph and brief description in a website operated by Walters Gardens, Inc., and on May 20, 2020 as a non-enabling photograph and brief description in the 2020-2021 Catalog by Walters Gardens, Inc., who obtained the plant and all information relating thereto, from the inventor. No plants of *Monarda* 'Berry Taffy' have been sold, in this country or anywhere in the world, nor has any disclosure of the new plant been made more than one year prior the filing date of this application, and such sale or disclosure within one year was either derived directly or indirectly from the inventor.

BACKGROUND OF THE INVENTION

The present invention relates to the new and distinct cultivar of Bee Balm, botanically known as *Monarda* 'Berry Taffy', and hereinafter also referred to solely by the cultivar 'Berry Taffy' or the "new plant." *Monarda* 'Berry Taffy' was the result of a controlled pollination in the summer of Jul. 24, 2014 in trial garden at a wholesale perennial nursery in Zeeland, Mich., USA. The female parent is a proprietary, unnamed, unreleased hybrid known as 12-27-8 and the specific male parent is a proprietary, unnamed, unreleased hybrid known as 12-59-12. The new plant was separated out for further evaluation in the summer of 2016 in the full sun trial gardens of the same nursery and assigned the breeder code 14-17-7. The new plant is the result of a planned breeding program of the inventor to produce new colors of flowers with superior mildew resistance, and improved compact habit. The new plant has been asexually propagated since 2016 by stem cuttings at the same nursery in the greenhouses in Zeeland, Mich., and the subsequent generations of asexually propagated plants found to be stable and identical to the original selection.

BRIEF SUMMARY OF THE PLANT

*Monarda* 'Berry Taffy' is unique from its parents and all other Bee Balm plants known to the inventor. The nearest comparison cultivars known to the inventor are 'Bubblegum Blast' U.S. Plant Pat. No. 27,497, 'Rockin' Raspberry' U.S. Plant Pat. No. 28,752, 'Grape Gumball' U.S. Plant Pat. No. 27,498 and 'Electric Neon Pink' U.S. Plant Pat. No. 30,347. 'Bubblegum Blast' has lighter hot pink flowers and the habit is significantly taller. 'Rockin' Raspberry' has a taller habit with similar anthocyanin pigmented foliage and the flowers are deep raspberry-purple. 'Grape Gumball' has a taller habit with similar anthocyanin pigmented foliage and the flowers are vibrant magenta. Both 'Rockin' Raspberry' and 'Grape Gumball' are later blooming. 'Electric Neon Pink' has flowers of a dark neon-pink color and is comparatively taller in habit.

The female parent is more spreading and taller in habit than the new plant and has deeper reddish flowers. The male parent has a shorter habit and the flowers are lighter pink colored.

*Monarda* 'Berry Taffy' is distinct from all Bee Balm plants known to the inventor. The following are traits of the new plant that in combination distinguish it from all other Bee Balm known to the inventor:

1. Deep-green, moderately-glossy, powdery mildew-tolerant foliage;
2. Short, compact, clumping, winter-hardy habit;

3. Compact, hot raspberry-pink flowers for a long period beginning late spring;
4. Bracts subtending inflorescences with deep reddish and wine coloration;
5. New leaves show a moderate to strong anthocyanin blush;
6. Flowering in dense verticils.

BRIEF DESCRIPTION OF THE DRAWINGS

The photographs of the new plant demonstrate the unique traits of *Monarda* 'Berry Taffy' and the overall appearance of the plant at three-years-old in the full sun trial garden of a nursery in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
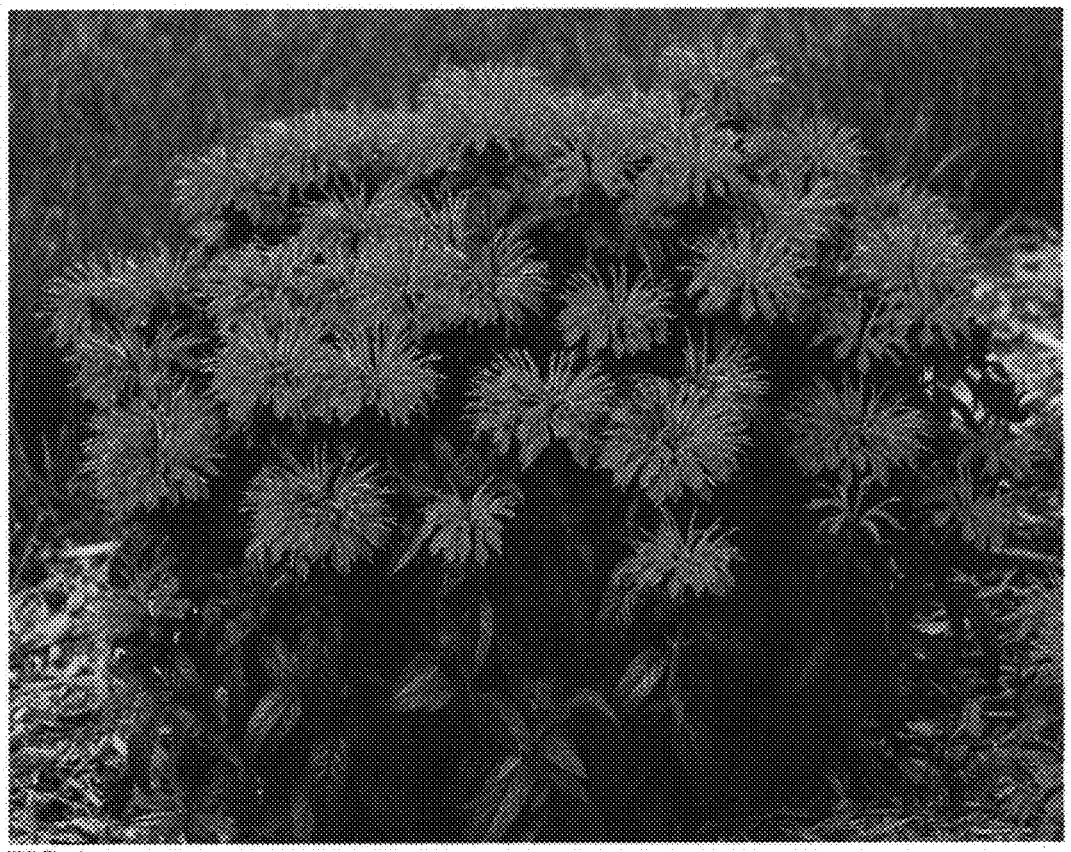
FIG. 1 shows the habit of the new plant in full flower.
Figure 2:
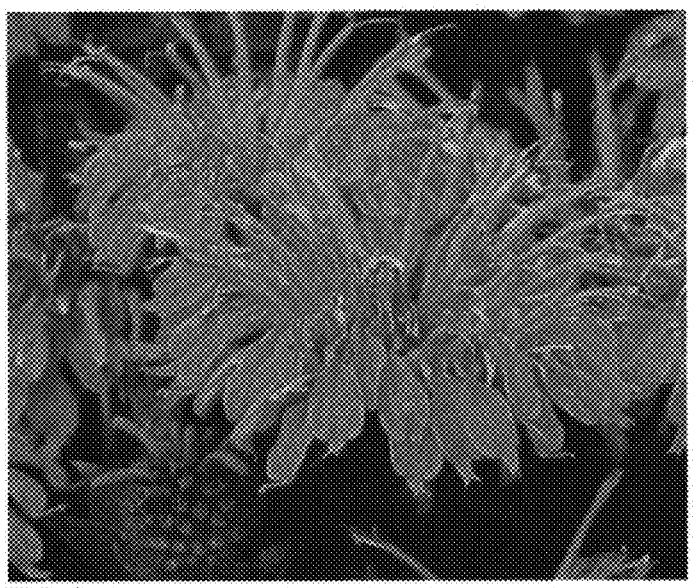
FIG. 2 shows a close-up of the flower of the new plant.

The following descriptions and color references are based on the 2015 edition of The Royal Horticultural Society Colour Chart except where common dictionary terms are used. *Monarda* 'Berry Taffy' has not been observed under all possible environments. The phenotype may vary slightly with different growing environments such as temperature, light, fertility, soil pH, moisture and maturity levels, but without any change in the genotype. The following observations and size descriptions are based on two-year-old greenhouse grown plants at a nursery in Zeeland, Mich. with supplemental fertilizer and water as needed.

Botanical classification: *Monarda* hybrid;

Parentage: The female (seed) parent is 12-27-8, an unreleased proprietary hybrid; the male (pollen) parent is 12-59-12, an unreleased, proprietary hybrid;

Plant habit: Hardy herbaceous perennial, compact, producing multiple stems spreading by short rhizomes near the base of the stems; foliage up to 38.0 cm tall, flowering to 40.0 cm tall and 43.0 cm wide; flowering begins late spring in Michigan and continuing for about 5 weeks;

Propagation: Stem cuttings;

Time to produce finished crop in 3.8 liter pots: About 7 to 9 weeks; moderate rate of growth;

Root: Fine, fibrous and freely branching; color creamy white to tan depending on soil type;

Leaves: Simple; lanceolate; opposite; margin serrated and ciliolate; puberulent above and below; highly lustrous adaxial, matte to slightly lustrous abaxial; narrowly acute apex; cordate to rounded base; to about 8.0 cm long and 3.0 cm wide, average about 6.2 cm long and 2.3 cm wide;

Leaf color: Young expanding leaves adaxial nearest RHS 137A, abaxial between RHS 147B and RHS 146A; older leaves adaxial blend between RHS N189A and RHS NN137A, abaxial nearest RHS NN137C; new leaves show a moderate to strong anthocyanin blush of nearest RHS 187A on adaxial surface;

Foliage Fragrance: pleasant lemony-herbal;

Veins: Pinnate; glabrous and slightly sunken adaxial, pubescent and costate abaxial;

Vein color: Adaxial midrib nearest RHS 195B with light blush of nearest RHS N186C, lateral pinnate veins and secondary veins between RHS N189A and RHS NN137A; abaxial midrib nearest RHS 145C with lateral pinnate veins nearest RHS 146D and secondary veins nearest RHS NN137A;

Petiole: Pubescent, slightly concaved above; to about 7.0 mm long and 2.0 mm across at base;

Petiole color: Adaxial nearest RHS N186C and abaxial nearest RHS 146D with a slight blush of nearest RHS N186C;

Stems: Quadrangular; puberulent; about 3.0 mm across at base; about 40 per plant; naturally branched at upper nodes; average 2.2 cm between nodes greater distally; 8 to 10 nodes per stem; average length about 22 cm;

Stem color: Nearest RHS 146C with faint anthocyanin expression in high light;

Flowers: Single labiate flowers arranged in mostly terminal verticils forming globular head about 7.8 cm across and 4.7 cm tall, opening from the center and progressing outwardly and down; attitude outwardly to upwardly; individual flowers to about 43.0 mm long to exserted stigma, 24.0 mm tall and about 8.0 mm across; individual flowers persisting about 5 days in Michigan; numerous, about 200 flowers per terminal head, fewer per axillary head;

Flower fragrance: Moderately spicy;

Buds one to two days prior to opening: Narrowly oblanceolate, arcuate downward; about 23.0 mm long and 3.0 mm across and 12.0 mm tall;

Bud color: Basal 5.0 mm nearest RHS NN155C, distal ventral portion nearest RHS 64B, distal dorsal region between RHS 61A and RHS 64A;

Petals: Bilabiate; arcuate downward; basal 23.0 mm fused into tube; split in two in the distal 15.0 mm; abaxial glandular to puberulent, adaxial glabrous; self-cleaning;

Upper labium: Rolled in middle portion about 15.0 mm long from fusion to apex, 3.0 mm tall, 2.5 mm across at base, about 4.0 mm across in middle when flattened; lanceolate with apex emarginate with three lobes about 1.0 mm long;

Lower labium: About 16.0 mm long from fusion to apex, apex comprising three lobes including two side lobes about 1.0 mm long and 2.0 mm across with rounded apex, center lobe about 4.0 mm long with emarginate apex in the distal 0.5 mm;

Petal color: Upper labium abaxial surface between RHS 61B and RHS 64A, adaxial surface between RHS 67A and RHS 67B; lower labium abaxial surface nearest between RHS 64B and RHS 64A, adaxial between RHS 64A and RHS 71B; corolla tube abaxial basal 5.0 mm nearest RHS NN155C, and distally between RHS 64C and RHS 64B, adaxial tube basal 5.0 mm nearest RHS NN155D and distally between RHS 70D and RHS 71D;

Androecium: Two;

*Filaments*.—Two; curved downward; adnate the inner corolla tube in the basal 18.0 mm and free in the distal 20.0 mm; about 0.5 mm diameter; color dorsal distally nearest RHS NN74D, middle dorsal portion nearest RHS 75D, basal dorsal and adnate portion nearest RHS N155B, and entire ventral portion nearest RHS N155B.

*Anther*.—Oblong elliptic, dorsifixed, longitudinal; 2.5 mm long by 1.0 mm wide; color nearest RHS 70A.

*Pollen*.—Abundant, elliptic to globose, less than 0.1 mm; color nearest RHS 11B.

Gynoecium: One; superior; about 41.0 mm long;

Pistil: One per flower; protruding about 7.0 mm beyond upper labium when mature;

Style: About 38.0 mm long and less than 0.5 mm diameter; arcuate along upper labium; color nearest RHS 70A in distal 5.0 mm transitioning to nearest RHS NN155D in middle and basal portion;

Stigma: Unevenly bifid in the distal 2.0 mm with one portion 1.0 mm and the other 2.0 mm long, about 0.2 mm in diameter; color nearest RHS 71A;

Ovary: Conical; about 1.0 mm tall by 0.7 mm across; color nearest RHS 150D;

Calyx: Tubular; consisting of five fused sepals; about 11.0 mm long and 2.5 mm diameter at apex;

Sepals: Five, apiculate apex; basal 10.0 mm fused forming calyx tube; margin ciliolate; about 11.0 mm long and 1.0 mm across at fusion; glabrous adaxial and abaxial; persistent;

Sepal color: Adaxial and abaxial basal 2.0 mm nearest RHS 145D, middle adaxial portion nearest RHS 145C and abaxial portion nearest RHS 146D, distal 3.0 mm abaxial portion nearest RHS 181D with veins nearest RHS 187B, and distal 3.0 mm adaxial portion nearest RHS 194C with veins nearest RHS 186B, apiculate apices on both adaxial and abaxial nearest RHS 187A;

Foliar bracts: Typically one set of six large bracts on the outside per inflorescence and one set of six smaller bracts in the middle and one set of about 24 to 30 smaller narrow bracts on the inside below each inflorescence; outer bracts lanceolate with acute apex and attenuate sessile base, ciliolate margin, glabrous adaxial, puberulent abaxial, flat to coarsely wavy, matte adaxial and abaxial, to 44.0 mm long and 17.0 mm wide in middle, color adaxial between RHS 187A and RHS N187A distally transitioning to nearest RHS NN137B in middle and RHS 145B at base, midrib nearest RHS 64A, color abaxial nearest RHS 137C; middle six bracts linear with narrowly acute apex and truncate base, ciliolate margin, glabrous adaxial and micro-puberulent abaxial, to about 18.0 mm long and 3.0 mm across near middle, adaxial color distal nearest RHS 187A, middle portion nearest RHS 64A and base nearest RHS145D, abaxial color nearest 146D in middle with apex strongly blushed with RHS 187A and base nearest RHS 145D; innermost bracts linear, narrowly acute apex and truncate base, ciliolate margin, adaxial and abaxial glabrous, to about 10.0 mm long and 0.7 mm across at base, color adaxial and abaxial nearest a blend between RHS 64A and RHS 187B;

Peduncle: Pubescent, stiff, strong, erect, quadrangular; to about 3.0 mm across and average 45.0 mm long above node; about 70 per plant; naturally branched at nodes;

Peduncle color: Between RHS 146C and RHS 146D;

Pedicel: About 2.0 mm long and 0.8 mm diameter; color nearest RHS 145B;

Fruit: Single nutlet, elliptical, about 1.3 mm long and 0.7 mm wide; color nearest RHS 200C;

Hardiness: The new plant grows best with plenty of moisture and adequate drainage; hardy to at least from USDA zone 4 through 8.

Disease and pest resistance: Demonstrated greater than average powdery mildew tolerance in side by side comparison with other *Monarda*.

I claim:

1. A new and distinct cultivar of hybrid ornamental Bee Balm plant, *Monarda* 'Berry Taffy', as herein described and illustrated.

* * * * *